(12) United States Patent
Bach

(10) Patent No.: US 11,504,401 B2
(45) Date of Patent: Nov. 22, 2022

(54) METHOD TO PREPARE A THERAPEUTIC BALM

(71) Applicant: Marina Bach, Miami, FL (US)

(72) Inventor: Marina Bach, Miami, FL (US)

( * ) Notice: Subject to any disclaimer, the term of this patent is extended or adjusted under 35 U.S.C. 154(b) by 177 days.

(21) Appl. No.: 17/089,989

(22) Filed: Nov. 5, 2020

(65) Prior Publication Data

US 2022/0133809 A1    May 5, 2022

(51) Int. Cl.

| | | |
|---|---|---|
| *A61K 36/906* | (2006.01) | |
| *A61K 36/53* | (2006.01) | |
| *A61K 36/752* | (2006.01) | |
| *A61K 36/00* | (2006.01) | |
| *A61K 36/282* | (2006.01) | |
| *A61K 36/38* | (2006.01) | |
| *A61K 36/45* | (2006.01) | |
| *A61K 35/644* | (2015.01) | |
| *A61K 36/28* | (2006.01) | |
| *A61K 36/534* | (2006.01) | |
| *A61K 36/515* | (2006.01) | |
| *A61K 36/67* | (2006.01) | |
| *A61K 36/76* | (2006.01) | |
| *A61K 36/9064* | (2006.01) | |
| *A61K 36/537* | (2006.01) | |
| *A61K 36/899* | (2006.01) | |
| *A61K 36/54* | (2006.01) | |
| *A61K 36/23* | (2006.01) | |
| *A61K 36/14* | (2006.01) | |
| *A61K 36/258* | (2006.01) | |
| *A61K 36/61* | (2006.01) | |
| *A61K 36/9066* | (2006.01) | |
| *A61K 36/736* | (2006.01) | |
| *A61K 36/738* | (2006.01) | |
| *A61K 36/815* | (2006.01) | |
| *A61K 36/88* | (2006.01) | |
| *A61K 36/889* | (2006.01) | |
| *A61K 36/185* | (2006.01) | |
| *A61K 36/73* | (2006.01) | |
| *A61K 36/48* | (2006.01) | |
| *A61K 36/882* | (2006.01) | |

(52) U.S. Cl.
CPC ............ *A61K 35/644* (2013.01); *A61K 36/14* (2013.01); *A61K 36/185* (2013.01); *A61K 36/23* (2013.01); *A61K 36/258* (2013.01); *A61K 36/28* (2013.01); *A61K 36/282* (2013.01); *A61K 36/45* (2013.01); *A61K 36/48* (2013.01); *A61K 36/515* (2013.01); *A61K 36/53* (2013.01); *A61K 36/534* (2013.01); *A61K 36/537* (2013.01); *A61K 36/54* (2013.01); *A61K 36/61* (2013.01); *A61K 36/67* (2013.01); *A61K 36/73* (2013.01); *A61K 36/736* (2013.01); *A61K 36/738* (2013.01); *A61K 36/752* (2013.01); *A61K 36/76* (2013.01); *A61K 36/815* (2013.01); *A61K 36/88* (2013.01); *A61K 36/882* (2013.01); *A61K 36/889* (2013.01); *A61K 36/899* (2013.01); *A61K 36/906* (2013.01); *A61K 36/9064* (2013.01); *A61K 36/9066* (2013.01); *A61K 2236/39* (2013.01)

(58) Field of Classification Search
None
See application file for complete search history.

(56) References Cited

U.S. PATENT DOCUMENTS

| | | | | |
|---|---|---|---|---|
| 6,132,788 | A * | 10/2000 | Zimlich, III | ............. C12G 3/07 |
| | | | | 426/429 |
| 2012/0072232 | A1* | 3/2012 | Frankham | .............. G16H 10/20 |
| | | | | 705/2 |
| 2017/0065659 | A1* | 3/2017 | Skorpen | .................. A61P 29/00 |

* cited by examiner

*Primary Examiner* — Michael Barker
*Assistant Examiner* — Randall O Winston

(57) ABSTRACT

A method to prepare a therapeutic balm is disclosed. A first phase solution is prepared in an oak barrel using a grain neutral spirit. The first phase is mixed for 10 minutes per day for a month to prepare a second phase solution. The second phase solution is filtered at least twice to prepare a filtrate. The filtrate and third phase components are mixed to prepare a third phase solution. The third phase solution is mixed with a distilled wine liquor to prepare a fourth phase solution. The fourth phase solution is mixed at least twice a day for a month to prepare a fifth phase solution. The fifth phase solution is mixed with cranberry juice, pomegranate juice, and raspberry juice to prepare a sixth phase solution. The sixth phase solution is stored in a ceramic bottle for a least six months at room temperature to prepare a therapeutic balm.

18 Claims, 1 Drawing Sheet

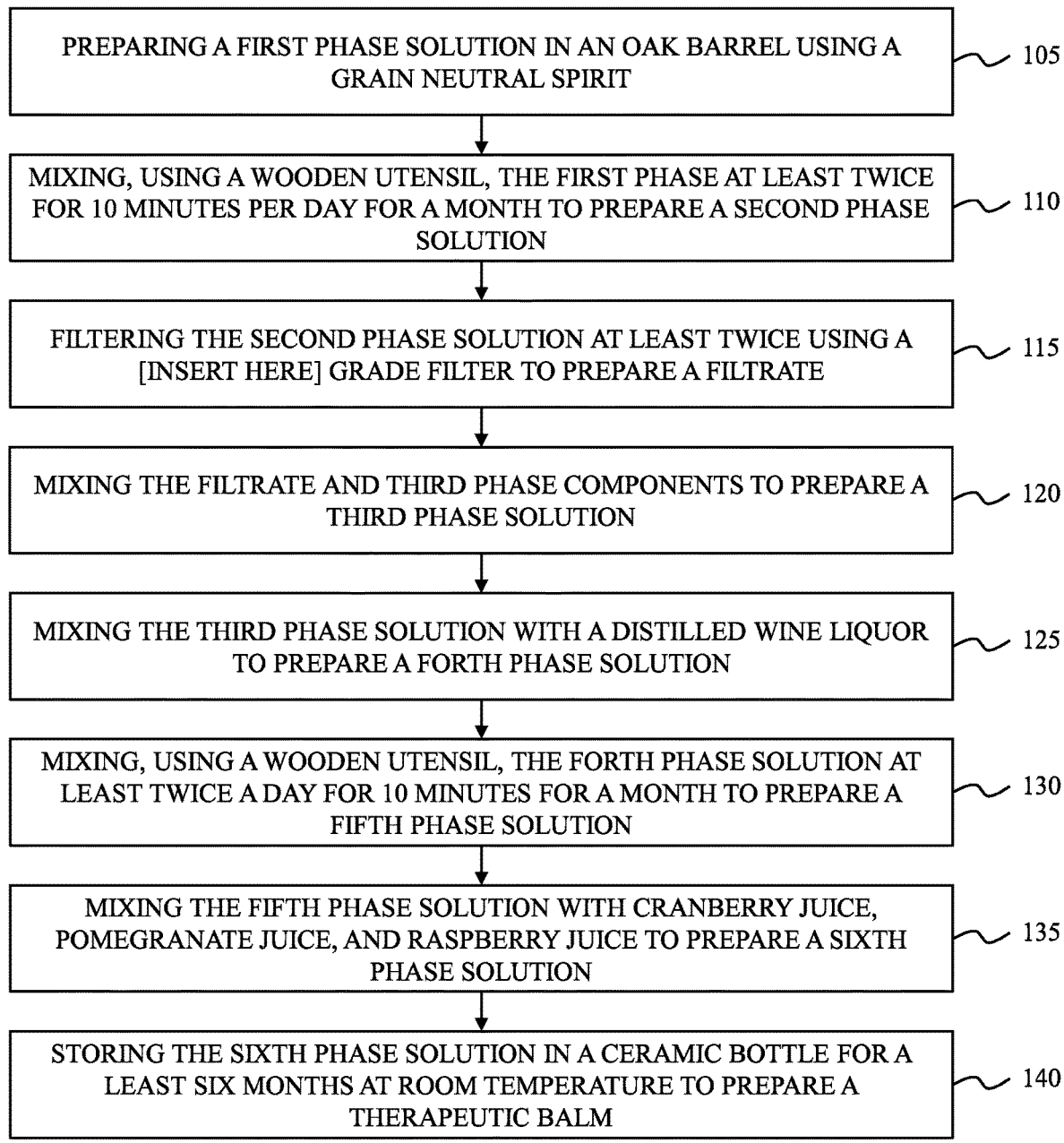

METHOD TO PREPARE A THERAPEUTIC BALM

FIELD OF THE INVENTION

The present disclosure relates generally to balms. More specifically, the present disclosure describes methods to prepare a therapeutic balm.

BACKGROUND OF THE INVENTION

From traditional Anglo-Saxon herbal tinctures to 5000-year-old Ayurvedic practices from the Indian subcontinent, all ancient cultures had natural healing practices that consisted entirely of organic ingredients and ancient wisdom. Without a multitude of over-hyped, under-tested pharmaceutical drugs at their disposal, early cultures relied on the knowledge passed down through generations to support their wellbeing and heal them in times of illness. Herbal remedies are plants used like a medicine. People use herbal remedies to help prevent or cure disease. They use them to get relief from symptoms, boost energy, relax, or lose weight.

BRIEF DESCRIPTION OF THE DRAWINGS

Some of the embodiments will be described in detail, with reference to the following figures, wherein like designations denote like members, wherein:

FIG. 1 illustrate process steps for preparing a therapeutic balm, according to some embodiments.

Unless otherwise specifically noted, articles depicted in the drawings are not necessarily drawn to scale.

DETAIL DESCRIPTIONS OF THE INVENTION

As a preliminary matter, it will readily be understood by one having ordinary skill in the relevant art that the present disclosure has broad utility and application. As should be understood, any embodiment may incorporate only one or a plurality of the above-disclosed aspects of the disclosure and may further incorporate only one or a plurality of the above-disclosed features. Furthermore, any embodiment discussed and identified as being "preferred" is considered to be part of a best mode contemplated for carrying out the embodiments of the present disclosure. Other embodiments also may be discussed for additional illustrative purposes in providing a full and enabling disclosure. Moreover, many embodiments, such as adaptations, variations, modifications, and equivalent arrangements, will be implicitly disclosed by the embodiments described herein and fall within the scope of the present disclosure.

Accordingly, while embodiments are described herein in detail in relation to one or more embodiments, it is to be understood that this disclosure is illustrative and exemplary of the present disclosure, and are made merely for the purposes of providing a full and enabling disclosure. The detailed disclosure herein of one or more embodiments is not intended, nor is to be construed, to limit the scope of patent protection afforded in any claim of a patent issuing here from, which scope is to be defined by the claims and the equivalents thereof. It is not intended that the scope of patent protection be defined by reading into any claim a limitation found herein that does not explicitly appear in the claim itself.

Thus, for example, any sequence(s) and/or temporal order of steps of various processes or methods that are described herein are illustrative and not restrictive. Accordingly, it should be understood that, although steps of various processes or methods may be shown and described as being in a sequence or temporal order, the steps of any such processes or methods are not limited to being carried out in any particular sequence or order, absent an indication otherwise. Indeed, the steps in such processes or methods generally may be carried out in various different sequences and orders while still falling within the scope of the present disclosure. Accordingly, it is intended that the scope of patent protection is to be defined by the issued claim(s) rather than the description set forth herein.

Additionally, it is important to note that each term used herein refers to that which an ordinary artisan would understand such term to mean based on the contextual use of such term herein. To the extent that the meaning of a term used herein—as understood by the ordinary artisan based on the contextual use of such term—differs in any way from any particular dictionary definition of such term, it is intended that the meaning of the term as understood by the ordinary artisan should prevail.

Furthermore, it is important to note that, as used herein, "a" and "an" each generally denotes "at least one," but does not exclude a plurality unless the contextual use dictates otherwise. When used herein to join a list of items, "or" denotes "at least one of the items," but does not exclude a plurality of items of the list. Finally, when used herein to join a list of items, "and" denotes "all of the items of the list."

The following detailed description refers to the accompanying drawings. Wherever possible, the same reference numbers are used in the drawings and the following description to refer to the same or similar elements. While many embodiments of the disclosure may be described, modifications, adaptations, and other implementations are possible. For example, substitutions, additions, or modifications may be made to the elements illustrated in the drawings, and the methods described herein may be modified by substituting, reordering, or adding stages to the disclosed methods. Accordingly, the following detailed description does not limit the disclosure. Instead, the proper scope of the disclosure is defined by the appended claims. The present disclosure contains headers. It should be understood that these headers are used as references and are not to be construed as limiting upon the subjected matter disclosed under the header.

Other technical advantages may become readily apparent to one of ordinary skill in the art after review of the following figures and description. It should be understood at the outset that, although exemplary embodiments are illustrated in the figures and described below, the principles of the present disclosure may be implemented using any number of techniques, whether currently known or not. The present disclosure should in no way be limited to the exemplary implementations and techniques illustrated in the drawings and described below.

The present disclosure includes many aspects and features. Moreover, while many aspects and features relate to, and are described in the context of methods to prepare a therapeutic balm, embodiments of the present disclosure are not limited to use only in this context.

From traditional Anglo-Saxon herbal tinctures to 5000-year-old Ayurvedic practices from the Indian subcontinent, all ancient cultures had natural healing practices that consisted entirely of organic ingredients and ancient wisdom. Without a multitude of over-hyped, under-tested pharmaceutical drugs at their disposal, early cultures relied on the knowledge passed down through generations to support their wellbeing and heal them in times of illness. Herbal remedies are plants used like a medicine. People use herbal remedies to help prevent or cure disease. They use them to get relief from symptoms, boost energy, relax, or lose weight.

The instant disclosure seeks to provide methods to prepare a therapeutic balm. The basis of the balm is an alcoholic tincture of herbs, such as Linden flowers (e.g., to stimulate the secretion of gastric juices and improve digestion), birch buds (e.g., to address beriberi and seasonal viral diseases). chamomile, various berries and roots. The disclosed balm has a vibrant deep shade, viscous consistency, as well as a pleasant taste and aroma. The disclosed balsam includes herbs, rhizomes, berries, fruits, essential oils, ethyl alcohol, brandy, and oil from Peru. The balm also includes spices and extracts that enhance the taste and strengthen the therapeutic benefits. The disclosed balsam can be used to address digestion issues, relieve pain, improve memory and sleep, reduce anxiety and stress, reduce the symptoms of the common cold, and boosts the immune system. The disclosed balm is also rich in antioxidants, which combats free radicals, and components that can enhance the breakdown of fats after a meal.

For usage, the therapeutic balm is preferably added to beverages (e.g., tea, coffee, or other hot/cold beverage) or food items (e.g., desserts). Users can digest 1-2 teaspoons weekly to achieve therapeutic results. FIG. 1 illustrate process steps for preparing the therapeutic balm, according to some embodiments. At Step 105, a first phase solution is prepared in an oak barrel using a grain neutral spirit.

Here, for each 1.75 L of the grain neutral spirit the first phase solution includes 2 g dried birdsfoot trefoil leaves, 4 g calamus root powder, 5 g dried mint leaves, 3.2 g dried mountain arnica flowers, 6 g dried wormwood, 4.8 g dried ginger root, 8 g dried gentian root, 4 g dried Melissa officinalis, 3.2 g dried linden flowers, 2.4 g black pepper powder, 2.4 g white bark powder, 2 g nutmeg powder, 3 g dried St. John's wort flowers and leaves, 8 g dried chamomile, 20 count dried cardamom pods, 3 g dried rosemary, 2 g dried lemon sorghum, 6 g dried oregano, 6 g cinnamon powder, 6 g bergamot powder, 6 g coriander powder, 6-8 count star anise fruit, 6 g juniper powder, 6 g dried clove, 6 g dried peppermint leaves, 8 g dried cumin seeds, 25 g 10-year aged ginseng root, 4 g dried basil leaves, 2 g dried eucalyptus leaves, 6 g turmeric powder, 6 g dried wintergreen leaves, 10-12 dehydrated black prunes, and 20 drops lemon oil.

At Step 110, using a wooden utensil, the first phase is mixed at least twice for 10 minutes per day for a month to prepare a second phase solution. At Step 115, the second phase solution is filtered at least twice to prepare a filtrate. For example, the second phase solution can be filtered using a food grade filter having, for example, 50-100 micron holes. At Step 120, the filtrate and third phase components are mixed to prepare a third phase solution. Here, for every 1.5 L of the filtrate the third phase components preferably include 60 g rose-hip powder, 40 g lemon balm powder, 60 g black currant powder, 40 g goji berry powder, 2 g Peruvian balsam, 16 oz. honey, 0.5 g dried saffron, 60 g bilberry extract powder, and 40 g acai berry powder. At Step 125, the third phase solution is mixed with a distilled wine liquor to prepare a forth phase solution. The distilled wine liquor includes an oak barrel aged brandy or an oak barrel aged cognac, according to preferred embodiments.

At Step 130, using a wooden utensil, the fourth phase solution is mixed at least twice a day for 10 minutes for a month to prepare a fifth phase solution. At Step 135, the fifth phase solution is mixed with cranberry juice, pomegranate juice, and raspberry juice to prepare a sixth phase solution.

Mixing the fifth phase solution with the cranberry juice, the pomegranate juice, and the raspberry juice preferably includes the following for every 3.5 L of fifth phase solution: 10 oz. cranberry juice, 10 oz. pomegranate juice; and 30 oz. raspberry juice. At Step 140, storing the sixth phase solution is stored in a ceramic bottle for a least six months at room temperature to prepare a therapeutic balm. Here, ceramic bottles reflect UV rays as well as minimize temperature changes and thereby preserve the therapeutic balm.

Although the disclosure has been explained in relation to its preferred embodiment, it is to be understood that many other possible modifications and variations can be made without departing from the spirit and scope of the disclosure.

What is claimed is:

1. A method to prepare a therapeutic balm, comprising:
    preparing a first phase solution in an oak barrel using a grain neutral spirit;
    mixing, using a wooden utensil, the first phase at least twice for 10 minutes per day for a month to prepare a second phase solution;
    filtering the second phase solution at least twice to prepare a filtrate;
    mixing the filtrate and third phase components to prepare a third phase solution;
    mixing the third phase solution with a distilled wine liquor to prepare a fourth phase solution;
    mixing, using a wooden utensil, the fourth phase solution at least twice a day for 10 minutes for a month to prepare a fifth phase solution;
    mixing the fifth phase solution with cranberry juice, pomegranate juice, and raspberry juice to prepare a sixth phase solution; and
    storing the sixth phase solution in a ceramic bottle for a least six months at room temperature to prepare a therapeutic balm.

2. The method of claim 1, wherein for each 1.75 L of the grain neutral spirit the first phase solution comprises:
    2 g dried birdsfoot trefoil leaves;
    4 g calamus root powder;
    5 g dried mint leaves;
    3.2 g dried mountain arnica flowers;
    6 g dried wormwood;
    4.8 g dried ginger root;
    8 g dried gentian root;
    4 g dried *Melissa officinalis;*
    3.2 g dried linden flowers;
    2.4 g black pepper powder;
    2.4 g white bark powder;
    2 g nutmeg powder;
    3 g dried St. John's wort flowers and leaves;
    8 g dried chamomile;
    20 count dried cardamom pods;
    3 g dried rosemary;
    2 g dried lemon sorghum
    6 g dried oregano;
    6 g cinnamon powder;
    6 g bergamot powder;
    6 g coriander powder;
    6-8 count star anise fruit;
    6 g juniper powder;
    6 g dried clove;
    6 g dried peppermint leaves;
    8 g dried cumin seeds;
    25 g 10-year aged ginseng root;
    4 g dried basil leaves;
    2 g dried eucalyptus leaves;
    6 g turmeric powder;

6 g dried wintergreen leaves;
10-12 dehydrated black prunes; and
20 drops lemon oil.

3. The method of claim 1, wherein for every 1.5 L of the filtrate the third phase components comprise:
   60 g rose-hip powder;
   40 g lemon balm powder;
   60 g black currant powder;
   40 g goji berry powder;
   2 g Peruvian balsam;
   16 oz. honey;
   0.5 g dried saffron;
   60 g bilberry extract powder; and
   40 g acai berry powder.

4. The method of claim 1, wherein the distilled wine liquor comprises an oak barrel aged brandy or an oak barrel aged cognac.

5. The method of claim 1, wherein mixing the third phase solution with the distilled wine liquor comprises mixing the third phase solution with 2 L of the distilled wine liquor for every 1.5 L of filtrate.

6. The method of claim 1, wherein for each 3.5 L of the fifth phase solution the cranberry juice comprises:
   10 oz. cranberry juice;
   the pomegranate juice comprises:
   10 oz. pomegranate juice; and
   the raspberry juice comprises:
   30 oz. raspberry juice.

7. The method of claim 2, wherein the 3 g dried St. John's wort flowers and leaves are substituted for 8 g dried Birch buds.

8. A method to prepare a therapeutic balm, comprising:
   preparing a first phase solution in an oak barrel using a 100% grain neutral spirit;
   mixing, using a wooden utensil, the first phase at least twice for 10 minutes per day for a month to prepare a second phase solution;
   filtering the second phase solution at least twice to prepare a filtrate;
   mixing the filtrate and third phase components to prepare a third phase solution;
   mixing the third phase solution with a distilled wine liquor to prepare a fourth phase solution;
   mixing, using a wooden utensil, the fourth phase solution at least twice a day for 10 minutes for a month to prepare a fifth phase solution;
   mixing the fifth phase solution with cranberry juice, pomegranate juice, and raspberry juice to prepare a sixth phase solution;
   storing the sixth phase solution in a ceramic bottle for a least six months at room temperature to prepare a therapeutic balm; and
   wherein
      the distilled wine liquor comprises an oak barrel aged brandy or an oak barrel aged cognac.

9. The method of claim 8, wherein for each 1.75 L of the grain neutral spirit the first phase solution comprises:
   2 g dried birdsfoot trefoil leaves;
   4 g calamus root powder;
   5 g dried mint leaves;
   3.2 g dried mountain arnica flowers;
   6 g dried wormwood;
   4.8 g dried ginger root;
   8 g dried gentian root;
   4 g dried *Melissa officinalis;*
   3.2 g dried linden flowers;
   2.4 g black pepper powder;
   2.4 g whitebark powder;
   2 g nutmeg powder;
   3 g dried St. John's wort flowers and leaves;
   8 g dried chamomile;
   20 count dried cardamom pods;
   3 g dried rosemary;
   2 g dried lemon sorghum
   6 g dried oregano;
   6 g cinnamon powder;
   6 g bergamot powder;
   6 g coriander powder;
   6-8 countstar anise fruit;
   6 g juniper powder;
   6 g dried clove;
   6 g dried peppermint leaves;
   8 g dried cumin seeds;
   25 g 10-year aged ginseng root;
   4 g dried basil leaves;
   2 g dried eucalyptus leaves;
   6 g turmeric powder;
   6 g dried wintergreen leaves;
   10-12 dehydrated black prunes; and
   20 drops lemon oil.

10. The method of claim 8, wherein for every 1.5 L of the filtrate the third phase components comprise:
   60 g rose-hip powder;
   40 g lemon balm powder;
   60 g black currant powder;
   40 g goji berry powder;
   2 g Peruvian balsam;
   16 oz. honey;
   0.5 g dried saffron;
   60 g bilberry extract powder; and
   40 g acai berry powder.

11. The method of claim 8, wherein mixing the third phase solution with the distilled wine liquor comprises mixing the third phase solution with 2 L of the distilled wine liquor for every 1.5 L of filtrate.

12. The method of claim 8, wherein for each 3.5 L of the fifth phase solution the cranberry juice comprises:
   10 oz. cranberry juice;
   the pomegranate juice comprises:
   10 oz. pomegranate juice; and
   the raspberry juice comprises:
   30 oz. raspberry juice.

13. The method of claim 9, wherein the 3 g dried St. John's wort flowers and leaves are substituted for 8 g dried Birch buds.

14. A method to prepare a therapeutic balm, comprising:
   preparing a first phase solution in an oak barrel using a 100% grain neutral spirit;
   mixing, using a wooden utensil, the first phase at least twice for 10 minutes per day for a month to prepare a second phase solution;
   filtering the second phase solution at least twice to prepare a filtrate;
   mixing the filtrate and third phase components to prepare a third phase solution;
   mixing the third phase solution with a distilled wine liquor to prepare a fourth phase solution;
   mixing, using a wooden utensil, the fourth phase solution at least twice a day for 10 minutes for a month to prepare a fifth phase solution;
   mixing the fifth phase solution with cranberry juice, pomegranate juice, and raspberry juice to prepare a sixth phase solution;

storing the sixth phase solution in a ceramic bottle for a least six months at room temperature to prepare a therapeutic balm; and wherein the distilled wine liquor comprises an oak barrel aged brandy or an oak barrel aged cognac; and for each 1.75 L of the grain neutral spirit the first phase solution comprises 2 g dried Birdsfoot trefoil leaves, 4 g calamus root powder, 5 g dried mint leaves, 3.2 g dried mountain arnica flowers, 6 g dried wormwood, 4.8 g dried ginger root, 8 g dried gentian root, 4 g dried Melissa officinalis, 3.2 g dried linden flowers, 2.4 g black pepper powder, 2.4 g whitebark powder, 2 g nutmeg powder, 3 g dried St. John's wort flowers and leaves, 8 g dried chamomile, 20 count dried cardamom pods, 3 g dried rosemary, 2 g dried lemon sorghum, 6 g dried oregano, 6 g cinnamon powder, 6 g bergamot powder, 6 g coriander powder, 6-8 count star anise fruit, 6 g juniper powder, 6 g dried clove, 6 g dried peppermint leaves, 8 g dried cumin seeds, 25 g 10-year aged ginseng root, 4 g dried basil leaves, 2 g dried eucalyptus leaves, 6 g turmeric powder, 6 g dried wintergreen leaves, 10-12 dehydrated black prunes, and 20 drops lemon oil.

15. The method of claim 14, wherein for every 1.5 L of the filtrate the third phase components comprise:

60 g rose-hip powder;
40 g lemon balm powder;
60 g black currant powder;
40 g goji berry powder;
2 g Peruvian balsam;
16 oz. honey;
0.5 g dried saffron;
60 g bilberry extract powder; and
40 g acai berry powder.

16. The method of claim 14, wherein mixing the third phase solution with the distilled wine liquor comprises mixing the third phase solution with 2 L of the distilled wine liquor for every 1.5 L of filtrate.

17. The method of claim 14, wherein for each 3.5 L of the fifth phase solution the cranberry juice comprises:

10 oz. cranberry juice;
the pomegranate juice comprises:
10 oz. pomegranate juice; and
the raspberry juice comprises:
30 oz. raspberry juice.

18. The method of claim 14, wherein the 3 g dried St. John's wort flowers and leaves are substituted for 8 g dried Birch buds.

* * * * *